United States Patent
Morganelli

(12) 
(10) Patent No.: US 6,193,967 B1
(45) Date of Patent: *Feb. 27, 2001

(54) BISPECIFIC REAGENTS FOR REDIRECTED TARGETING OF HUMAN LIPOPROTEINS

(76) Inventor: Peter M. Morganelli, Woodhaven Dr. 21, White River Junction, VT (US) 05001

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/947,037

(22) Filed: Oct. 8, 1997

Related U.S. Application Data

(60) Division of application No. 08/155,114, filed on Nov. 19, 1993, now Pat. No. 5,762,930, which is a continuation-in-part of application No. 07/955,681, filed on Oct. 2, 1992, now abandoned.

(51) Int. Cl.[7] .................................................. A61K 39/395
(52) U.S. Cl. ..................................... 424/136.1; 424/143.1; 424/145.1; 424/158.1; 424/178.1
(58) Field of Search ......................... 530/388.22, 388.25, 530/387.3, 391.1, 806, 809; 424/143.1, 136.1, 138.1, 145.1, 158.1, 178.1; 435/240.2, 240.26, 240.27

(56) References Cited

U.S. PATENT DOCUMENTS

| | | |
|---|---|---|
| 4,470,925 | 9/1984 | Auditore-Hargreaves . |
| 4,676,980 | 6/1987 | Segal et al. . |
| 4,900,726 | 2/1990 | Tipton et al. . |
| 4,900,744 | 2/1990 | Billheimer et al. . |
| 4,954,617 * | 9/1990 | Fanger et al. ...................... 530/387 |
| 5,196,324 | 3/1993 | Bumol et al. . |
| 5,635,600 | 6/1997 | Fanger et al. . |

FOREIGN PATENT DOCUMENTS

| | | |
|---|---|---|
| 0308936 | 3/1989 | (EP) . |
| WO 91/00360 | 1/1991 | (WO) . |
| WO 91/03493 | 3/1991 | (WO) . |
| WO 91/05871 | 5/1991 | (WO) . |
| WO 92/05793 | 4/1992 | (WO) . |
| WO 92/08802 | 5/1992 | (WO) . |
| WO 94/10332 | 5/1994 | (WO) . |
| WO 95/09917 | 4/1995 | (WO) . |

OTHER PUBLICATIONS

Fanger, M.W. et al., Proceedings of the American Association for Cancer Research 32:489–490, Mar. 1991.*
Fanger et al., Trends in Biotechnology, vol. 9, pp. 375–380, Nov., 1991.*
Silberman et al., Biochemistry (1987) 26, 18, 5833–43, 1987.*
International Search Report, International Application No. PCT/US 93/09556, Mailing Date Feb. 22, 1994.

Anderson et al. "Monoclonal antibodies to Fc Receptors for IgG on Human Mononuclear Phagocytes" *The Journal of Biological Chemistry* 261(27):12856–12864 (1986).
Anderson, C.L et al. "Stimulation of Superoxide Production by a Monoclonal Antibody (mab) Against the High Affinity IgG Fc Receptor (FcRI) of U937 Cells" *Fed. Proc.* 45: 714, Abstract #3247 (1986).
Araki, N. et al. "Microquantification of Cholesterol and Cholesteryl Esters in Rat Peritoneal Macrophages by Reverse–Phase High–Performance Liquid Chromatography" *Analytical Biochemistry* 185:339–345 (1990).
Badimon, J.J. et al. "Role of High Density Lipoproteins in the Regression of Atherosclerosis" *Supplement to Circulation, Progression–Regression of Atherogenesis: Molecular, Cellular and Clinical Bases, American Heart Association* 86(6): III–86–III–93 (1992).
Ball, E. et al. "Initial Trial of Bispecific Antibody–Mediated Immunotherapy of CD15–Bearing Tumors: Cytotoxicity of Human Tumor Cells Using a Bispecific Antibody Comprised of Anti–CD15 (MoAb PM81) and Anti–CD64/FcγRI (MoAb 32)" *Journal of Hematotherapy* 1: 85–94 (1992).
Berg et al. "Bispecific Antibodies that Mediate Killing of Cells Infected with Human Immunodeficiency Virus of any Strain" *PNAS USA* 88:4723–4727 (1991).
Bernini, F. et al. "Enhanced Catabolism of Low Density Lipoproteins in Rat by Lactosaminated Fab Fragment" *The Journal of Biological Chemistry* 261(20):9294–9299 (1986).
Bernini, F. et al. "Lactosaminated Fab Fragments Specific for Low Density Lipoproteins/Hepatocyte Targeting and Hypolipoproteinemic Activity" *Arteriosclelerosis* 8(6):825–831 (1988).
Bijsterbosch et al. "Enhanced Hepatic Uptake and Processing of Cholesterol Esters from Low Density Lipoprotein by Specific Lactosaminated Fab Fragments" *Arteriosclerosis and Thrombosis* 11(6): 1806–1813 (1991).

(List continued on next page.)

Primary Examiner—Laurie Scheiner
(74) Attorney, Agent, or Firm—Lahive & Cockfield, LLP; Jane E. Remillard, Esq.; Jeanne M. DiGiorgio, Esq.

(57) ABSTRACT

Bispecific molecules which react both with an Fcγ receptor for immunoglobulin G (IgG) of human effector cells and with either human low density lipoprotein (LDL), or fragment thereof, or human high density lipoprotein (HDL), or a fragment thereof, are disclosed. The bispecific molecules bind to an Fcγ receptor without being blocked by the binding of IgG to the same receptor. The bispecific molecules having a binding specificity for human LDL are useful for targeting human effector cells for degradation of LDL in vivo. The bispecific molecules of the present invention which have a binding specificity for human HDL are useful for targeting human HDL to human effector cells such that the HDL takes up cholesterol from the effector cells. Also disclosed are methods of treating atherosclerosis using these bispecific molecules.

12 Claims, 4 Drawing Sheets

OTHER PUBLICATIONS

Brennan, M. et al. "Preparation of bispecific Antibodies by Chemical Recombination of Monoclonal Immunoglobulin $G_1$ Fragments" *Science* 229:81–83 (1985).

Castelli, W.P. et al. "HDL Cholesterol and Other Lipids in Coronary Heart Disease: the Cooperative Lipoprotein Phenotyping Study" *Circulation, An Official Journal of the American Heart Association, Inc.* 55(5): 767–772 (1977).

Clark, M et al. "Use of Bispecific Monoclonal Antibodies to Treat Hematological Malignancies: a Model System Using CD3 Transgenic Mice" Bispecific Antibodies and Targeted Cellular Cytotoxicity: Second International Conference, Seilliac, France—Oct. 9–13, 1990, Romet–Lemonne, J.L. et al., eds.:243–247.

Connor, R.I. et al. "Fc Receptors for IgG (FcγRs) on Human Monocytes and Macrophages are not Infectivity Receptors for Human Immunodeficiency Virus Type 1 (HIV–1): Studies Using Bispecific Antibodies to Target HIV–1 to Various Myeloid Cell Surface Molecules, Including the Fc γR" *PNAS USA* 88:9593–9597 (1991).

de Leij, L. et al. "Intrapleural and Intraperitoneal Application of Bispecific antibody Retargeted Lymphocytes to Cancer Patients" Bispecific Antibodies and Targeted Cellular Cytotoxicity: Second International Conference, Seilliac, France—Oct. 9–13, 1990, remot–Lemonne, J.L. et al., eds.:249–251.

Ericson, S.G. et al. "The Effect of Recombinant Human Interleukin–3 and Recombinant Human Granulocyte–Macro–Phage Colony–Stimulating Factor on Fcγ Receptor Expression and Antibody–Dependent Cellular Cytotoxicity of Hematopoietic Progenitor Cells During in Vitro Myeloid Maturation" *Experimental Hematology* 22: 283–289 (1994).

Fanger, M.W. et al. "Bispecific Antibodies" *Critical Reviews in Immunology* 12 (3–4): 101–124 (1992).

Fanger, M.W. et al. "Bispecific Antibodies for Targeted Cellular Cytotoxicity" *Trends in Biotechnology* 9:375–380 (1991).

Fanger, M.W. et al. "Cytotoxicity Mediated by Human Fc Receptors for IgG" *Immunology Today* 10(3):92–99 (1989).

Fanger, M.W. et al. "Fcγ Receptors in Cancer and Infectious Disease" *Immunol. Res.* 11:203–216 (1992).

Fanger, M. et al. "The Use of Bispecific Antibody in the Therapy of Tumors" *Proceedings of the American Association for Cancer Research* 32:489–490 (1991).

Garrido, M.A. et al. "Targeting Human T–Lymphocytes with Bispecific Antibodies to React against Human Ovatian Carcinoma Cells Growing in nu/nu Mice" *Cancer Research* 50:4227–4232 (1990).

Gibbs, W. W. "Try, Try Again" *Science and Business, Scientific American* Jul.:101–103 (1993).

Gilliland, L.K. et al. "Universal Bispecific Antibody for Targeting Tumor Cells for Destruction by Cytotoxic T Cells" *PNAS USA* 85:7719–7723 (1988).

Graziano et al. "FcγR–Mediated Killing by Eosinophils" *The Journal of Immunology* 142:230–235 (1989).

Griffith et al. "Low Density Lipoprotein Metabolism by Human Macrophages Activated with Low Density Lipoprotein Immune Complexes: A Possible Mechanism of Foam Cell Formation" *The Journal of Experimental Medicine* 168: 1041–1059 (1988).

Guyre, P.M. et al. "Monoclonal Antibodies that Bind to Distinct Epitopes on FcγRI are Able to Trigger Receptor Function" *The Journal of Immunology* 143(5): 1650–1655 (1989).

Guyre, P.M. et al. "Recombinant Immune Interferon Increases Immunoglobulin G Fc Receptors on Cultured Human Mononuclear Phagocytes" *Journal of Clinical Investigation* 72:393–397 (1983).

Harris, W. et al. "Therapeutic Antibodies—The Coming of Age" *Tibtech* 11:42–44 (1993).

Hird, V. et al. "Immunotherapy with Monoclonal Antibodies" *Genes and Cancer* Edited by D. Carney and K. Sikora, Chapter 17, pp. 183–189 (1990).

Isturiz, M.A. et al. "Two Different Fcγ Receptor–Dependent Cytotoxic Mechanisms Triggered by Monoclonal Immunoglobulins" *Immunology Letters* 29: 271–276 (1991).

Jung, G. et al. "Target Cell–Induced T cell Activation with Bi– and Trispecific Antibody Fragments" *Eur. J. Immunol.* 21:2431–2435 (1991).

Karawajew, L. et al. "Flow Sorting of Hybrid Hybridomas Using the DNA Stain Hoechst 33342" *The Journal of Immunological Methods* 129(2):277–282 (1990).

Karpovsky, B. et al. "Production of Target–Specific Effector Cells Using Hetero–Cross–Linked Aggregates Containing Anti–Target Cell and Anti–Fcγ Receptor Antibodies" *Journal of Experimental Medicine* 160: 1686–1701 (1984).

Liu, M.A. et al. "Heteroantibody Duplexes Target Cells for Lysis by Cytotoxic T Lymphocytes" *PNAS* 82: 8648–8652 (1985).

Liu, M.A. et al "Hormone Conjugated with Antibody to CD3 Mediates Cytotoxic T Cell Lysis of Human Melanoma Cells" *Science* 239:395–398 (1988).

Looney, R.J. et al. "Human Monocytes and U937 Cells Bear Two Distinct Fc Receptors for IgG" *The Journal of Immunology* 136(5):1641–1647 (1986).

Lopes–Virella, M. et al. "Enhanced Uptake and Impaired Intracellular Metabolism of Low Density Lipoproten Complexed with Anti–Low Density Lipoprotein Antibodies" *Arteriosclerosis and Thrombosis* 11(5):1356–1367 (1991).

Lubeck, M.D. et al. "The Interation of Murine IgG Subclass Proteins with Human Monocyte Fc Receptors" *The Journal of Immunology* 135(2):1299–1304 (1985).

Mabondzo, A. et al. "Bispecific Antibody Targeting of Human Immunodeficiency Virus Type 1 (HIV–1) Glycoprotein 41 to Human Macrophages through the Fc IgG Receptor I Mediates Neutralizing Effects in HIV–1 Infection" *The Journal of Infectious Diseases* 166:93–99 (1992).

Morganelli, P.M. et al. "Redirected Targeting of LDL to Human Monocyte Fcgamma Receptors with Bispecific Antibodies" *Arteriosclerosis and Thrombosis* 12(10):1131–1138 (1992).

Nitta, T. et al. "Preliminary Trial of Specific Targeting Therapy against Malignant Glioma" *The Lancet* 335:368–371 (1990).

Palinski et al. "Immunization of Low Density Lipoproten (LDL) Receptor–Deficient Rabbits with Homologous Malondialdehyde–Modified LDL Reduces Atherogenesis" *PNAS USA* 92:821–825 (1995).

Perez, P. et al. "Specific Targeting of Cytotoxic T Cells by Anti–Target Cell Antibody" *Nature* 316: 354–356 (1985).

Sarmay, G. et al. "Mapping and Comparison of the Interaction Sites on the Fc Region of IgG Responsible for Triggering Antibody Dependent Cellular Cytotoxicity (ADCC) through Different Types of Human Fcγ Receptor" *Molecular Immunology* 29(5): 633–639 (1992).

Shen, L. et al. "Direct Stimulation of ADCC by Cloned Gamma Interferon is not Ablated by Glucocorticoids: Sstudies Using a Human Monocyte–like Cell Line (U–937)" *Molecular Immunology* 21(2): 167–173 (1984).

Shen, L. et al. "Heteroantibody–Mediated Cytotoxicity: Antibody to the High Affinity Fc Receptor for IgG Mediates Cytotoxicity by Human Monocytes that is Enhanced by Interferon–γ and is not Blocked by Human IgG" *The Journal of Immunology* 137(11): 3378–3382 (1986).

Shen, L et al. "Polymorphonuclear Leukocyte Function Triggered through the High Affinity Fc Receptor for Monomeric IgG" *The Journal of Immunology* 139:534–538 (1987).

Steinberg, D. et al. "Beyond Cholesterol: Modifications of Low–Density Lipoprotein that Increase its Atherogenicity" *The New England Journal of Medicine* 320(14):915–924 (1989).

Titus et al. "Human T Cells Targeted with Anti–T3 Cross–Linked to Antitumor Antibody Prevent Tumor Growth in Nude Mice" *The Journal of Immunology* 138(11):4018–4022 (1987).

Titus, J.A. et al. "Human K/Natural Killer Cells Targeted with Hetero–Cross–Linked Antibodies Specifically Lyse Tumor Cells in Vitro and Prevent Tumor Growth In Vivo" *The Journal of Immunology* 139:3153–3158 (1987).

Valerius, T. et al. "Involvement of the High–Affinity Receptor for IgG (FcγRI; CD64) in Enhanced Tumor Cell Cytotoxicity of Neutrophils During Granulocyte Colony–Stimulating Factor Therapy" *Blood* 82(3): 931–939 (1993).

van de Winkel, J. et al. "Human IgG Fc Receptor Heterogeneity: Molecular Aspects and Clinical Implications" *Immunology Today* 14(5): 215–221 (1993).

Waldmann, T. "Monoclonal Antibodies in Diagnosis and Therapy" *Science* 252: 1657–1662 (1991).

* cited by examiner

BISPECIFIC REAGENTS FOR REDIRECTED TARGETING OF HUMAN LIPOPROTEINS

RELATED APPLICATIONS

This application is a divisional application of Ser. No. 08/155,114 filed on Nov. 19, 1993 now U.S. Pat. No. 5,762,930, which in turn is a continuation-in-part application of Ser. No. 07/955,681 filed on Oct. 2, 1992, abandoned. The contents of all of the aforementioned application(s) are hereby incorporated by reference.

BACKGROUND OF THE INVENTION

Atheromatous lesions consist of numerous cellular and acellular elements. Macrophages are a major constituent of these lesions as they develop into characteristic cholesteryl ester-laden foam cells (Ross, R. (1986) *New England J. Med.* 314:488–500; Munro, J. M. and Cotran, R. S. (1988) *Laboratory Invest.* 58:249–261). For macrophages, foam cell development during atherogenesis is ultimately dependent upon uptake of various forms of low density lipoprotein (LDL) (reviewed in Brown, M. S. and Goldstein, J. L. *Ann. Rev. Biochem.* 52:223–261). Of late, emphasis has been placed on the importance of the interaction of chemically modified or oxidized LDL with macrophage scavenger receptors (reviewed in Steinberg, D., et al. (1988) *New England J. Med.* 320:915–924), which may occur during atherogenesis in vivo (Steinberg, D., et al. (1988) *New England J. Med.* 320:915–924; Haberland, M. E., et al. (1988) *Science* 241:215–218; Palinski, W., et al. (1989) *Proc. Natl. Acad. Sci. USA* 86:1372–1376; Rosenfeld, M. E., etal. (1990) *Arteriosclerosis* 10:336–349; Boyd, H. C., et al. (1990) *Am. J. Path.* 135:815–825).

Foam cell development may also be influenced by the interaction of lipoproteins with pathways other than those associated with scavenger receptors. In particular, recent studies have shown that immune complexes consisting of LDL bound to anti-LDL antibodies (LDL-IC) can cause foam cell development in vitro through interaction with IgG Fc receptors (FcγR) when administered to both mouse (Klimov, A. N., et al. (1985) *Atherosclerosis* 58:1–15) and human macrophages (Lopes-Virella, M. F., et al. (1991) *Arteriosclerosis and Thrombosis* 11:1356–1367; Griffith, R. L., et al. (1988) *J. Exp. Med.* 168:1041–1059). LDL-IC (reviewed in Orekhov, A. N. (1991) *Curr. Opin. Lipidology* 2:329–333) consisting of antibodies bound to either native or oxidized LDL exist in numerous situations in vivo (Szondy, E., et al. (1983) *Atherosclerosis* 49:69–77; Parums, D. V., et al. (1990) *Arch. Pathol. Lab. Med.* 114:383–387; Beaumont, J. L., et al. (1988) *Atherosclerosis* 74:191–201; Kigore, L. L., et al. (1985) *J. Clin. Invest.* 76:225–232), and in several cases have been correlated with abnormalities of lipid metabolism and atherosclerosis (Szondy, E., et al., supra; Parums, D. V., et al., supra; Beaumont, J. L., et al., supra; Kigore, L. L., et al., supra; Cohen, L., et al. (1966) *Am. J. Med.* 40:299–316).

In contrast to the role of LDL in foam cell development, human high density lipoprotein (HDL) may play a role in preventing foam cell development. HDL is known to play a role in cholesterol efflux from extrahepatic tissues, such as vascular tissue, to the liver where it can be metabolized. See, e.g., Badimon, J. J. et al. (1992) *Circulation* (Supp. III) 86(6):III-86-III-94; Castell, W. P. et al (1977) *Circulation* 55(5):767–772. Moreover, it has been shown that plasma HDL both inhibits the development of experimental atherosclerosis and induces regression of the lipid infiltration into vessel (e.g., aortic) walls. Badimon, J. J. et al., supra.

Human Fcγ receptors (FcγR) (reviewed in Fanger, M. W., et al. (1989) *Immunology Today* 10:92–99), of which there are three structurally and functionally distinct types (i.e., FcγRI, FcγRII and FcγRIII), are well-characterized cell surface glycoproteins that mediate phagocytosis or antibody-dependent cell cytotoxicity (ADCC) of immunoglobulin G (IgG) opsonized targets.

Bispecific antibody technology has been used to evaluate the function of specific FcγR. Investigators have shown that FcγR are the only cell surface molecules on myeloid cells capable of triggering phagocytic or cytotoxic function (Shen, L., et al. (1986) *J. Immunol.* 137:3378–3382; Shen, L. et al. (1987) *J. Immunol.* 139:534–538; Connor, R. I., et al. (1990) *J. Immunol.* 145:1483–1489; Anderson, C. L., et al. (1990) *J. Exp. Med.* 171:1333–1345). However, clear differences in the functional ability of the different FcγR could be demonstrated that was dependent not only on the FcγR class or isoform but on the state of activation and differentiation of the cell (Fanger, M. W., et al. (1989) *Immunology Today* 10:92–99; Van de Winkel, J. G. and Anderson, C. L. (1991) *J. Leukocyte Biol.* 49:511–524).

SUMMARY OF THE INVENTION

This invention pertains to bispecific molecules which can bind human low density lipoprotein (LDL) and/or which can simultaneously target human LDL for ingestion and metabolic degradation by effector cells such as monocytes, macrophages, eosinophils, granulocytes, platelets and neutrophils. The bispecific molecules of this invention have a first binding specificity for human LDL and a second binding specificity for an Fcγ receptor for immunoglobulin G (IgG), such as the human Fcγ receptors FcγRI, FcγRII and FcγRIII. In a preferred embodiment, such bispecific molecules are capable of binding to IgG-occupied Fcγ receptors on effector cells. For specifically targeting FcγRI, it is preferred that the bispecific molecule have a binding specificity for an epitope on the receptor which is distinct from the Fc ligand binding domain of the receptor for the Fc region of IgG.

This invention further pertains to bispecific molecules which can bind human high density lipoprotein (HDL) and/or which can simultaneously target HDL to effector cells such as macrophages or macrophage-derived foam cells for HDL uptake of cholesterol from the effector cells. The bispecific molecules of this invention have a first binding specificity for human HDL and a second binding specificity for an Fcγ receptor for immunoglobulin G (IgG), such as the human Fcγ receptors FcγRI, FcγRII and Fcγ RIII. In a preferred embodiment, such bispecific molecules are capable of binding to IgG-occupied Fcγ receptors on effector cells. For specifically targeting FcγRI, it is preferred that the bispecific molecule have a binding specificity for an epitope on the receptor which is distinct from the Fc ligand binding domain of the receptor for the Fc region of IgG.

A bispecific molecule of the invention can be a bispecific antibody (i.e., a single antibody or antibody fragment with a dual binding specificity), a heteroantibody (i.e., an aggregate of two or more antibodies or antibody fragments, each having a different binding specificity) or a single chain bispecific polypeptide. In general, a bispecific antibody, heteroantibody or single chain bispecific polypeptide comprises: at least one antigen binding region derived from an anti-Fc receptor antibody whose binding to human Fc receptor is not blocked by human IgG; and at least one antigen binding region specific for a human lipoprotein, such as human LDL or human HDL.

The binding of a bispecific molecule of the present invention, e.g., a bispecific molecule having a binding specificity for human LDL, to an appropriate effector cell results in a targeted effector cell, i.e., an effector cell to which is bound a bispecific antibody or heteroantibody containing antigen binding regions specific for human LDL. The targeted effector cells can be used to bring about phagocytosis of LDL by the effector cells. The binding of another bispecific molecule of the present invention, e.g., a bispecific molecule having a binding specificity for human HDL, to an appropriate effector cell, e.g., a macrophage-derived foam cell, results in a targeted effector cell, i.e., an effector cell to which is bound a bispecific antibody or heteroantibody containing antigen binding regions specific for human HDL. The targeted effector cells can be used to bind HDL, thereby allowing uptake and/or removal of cholesterol from the effector cells.

The bispecific molecules of this invention have therapeutic as well as diagnostic applications. As therapeutic agents, the bispecific molecules can be administered to an individual alone, or pre-bound to effector cells having the appropriate Fc receptor prior to administration. In either form, the bispecific molecules of the present invention which have a binding specificity for human HDL are administered in an amount sufficient to induce phagocytosis of human LDL to thereby reduce LDL levels in the individual. The bispecific molecules of the present invention which have a binding specificity for human HDL are administered in an amount sufficient to induce uptake of cholesterol by human HDL from the effector cells, to thereby reduce cholesterol levels and/or atherosclerotic lesions in the individual. Bispecific molecules of the invention can also be used in conjunction with other molecules such as cytokines (e.g., interferon-γ) which can activate or enhance their therapeutic potential.

As diagnostic agents, the bispecific molecules having a binding specificity for human LDL can be cultured ex vivo with an individual's white blood cells (e.g., monocytes or macrophages), to evaluate the capacity or tendency of such cells to accumulate cholesteryl ester and develop into foam cells. The tendency of white blood cells of the individual to develop into foam cells indicates that the individual is at risk of developing atherosclerosis.

DETAILED DESCRIPTION OF THE INVENTION

Figure 1A:
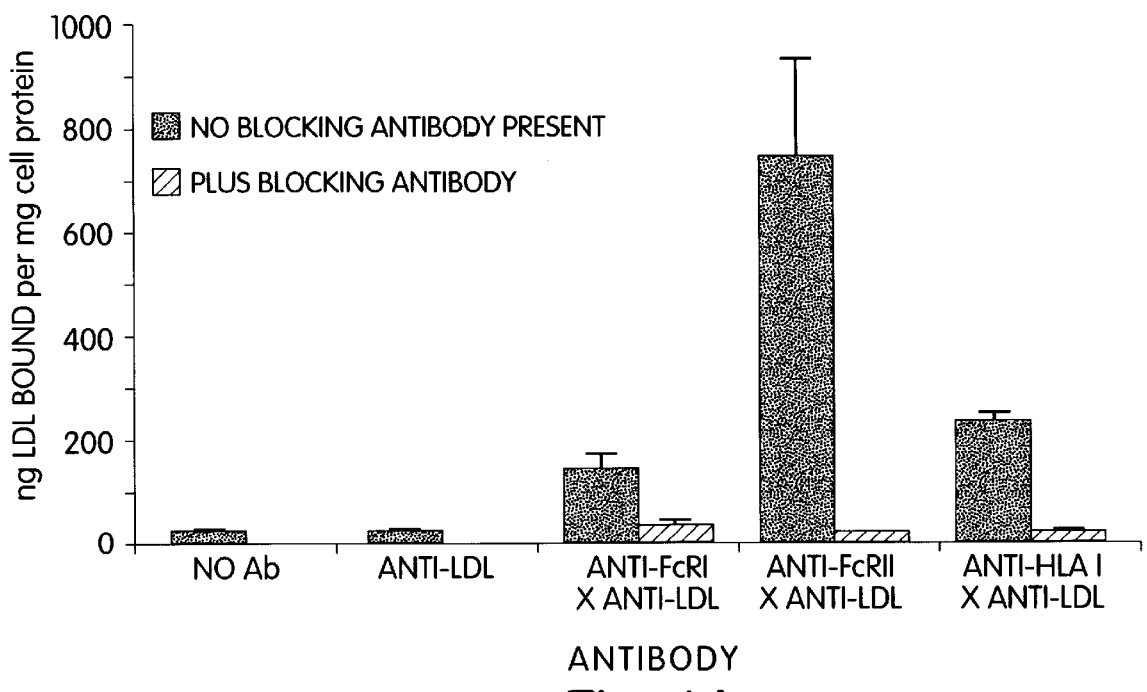
FIG. 1 is a graphic representation of the binding of $^{125}$I-LDL to human monocyte receptors mediated through bispecific molecules. Monocytes (A) or polymorphonuclear cells (PMN) (B) were treated with 25 μg/ml of the indicated bispecific antibody and 100 μg/ml of $^{125}$I-LDL plus equivalent amounts of anti-LDL alone. To show specificity, the binding of bispecific antibodies was also done in the presence of an excess amount (0.5 mg/ml) of the corresponding unconjugated anti-FcγR or anti-HLA Class I antibody (hatched bars). Shown are the means±SD of triplicate measurements of ng $^{125}$I-LDL bound per mg cell protein.

There are three structurally and functionally distinct types of human FcγR receptors, FcγRI, FcγRII and FcγRIII. FcγRI is a 70 kDa glycoprotein which binds to monovalent IgG with high affinity, and an equilibrium dissociation constant (Kd) of $10^{-8}$–$10^{-9}$ M for human IgG1 and IgG3, and mouse IgG2a and IgG3 (Kurlander et al. (1982) *J. Clin. Invest.* 69:1–8; Jones et al. (1985) *J. Immunol.* 135:3348–3353). Two different epitopes on FcγRI, each distinct from the ligand-binding site, have been defined using mAb 32 and mAb 22, (Guyre, P. M., et al., submitted) and the binding of these mAbs to FcγRI is not blocked by human IgG or by immune complexes.

FcγRII (CDw32) is a 40 kDa glycoprotein (Anderson, C. L. (1982) *J. Exp. Med.* 156:1794–1806). Two forms of FcγRII were identified based on functional assays and biochemical analysis (Anderson, C. L. and Looney, R. J. (1986) *Immunol. Today* 7:264–266). Recent cDNA cloning experiments support the concept of multiple receptor subtypes, as cDNAs have been isolated that identify at least three related molecules possessing identical extracellular, but different cytoplasmic domains (Mellman, 1. (1988) *Current Opin. Immunol.* 1: 16–25; Stengelin, S., et al. (1988) *EMBO J.* 17:1053–1059). All forms of FcγRII have low affinity for monovalent human IgG1, and thus appear to be specific for immune complexes and opsonized particles.

FcγRIII (CD16) also has low affinity for monomeric IgG, and was originally identified as a 50–70 kDa glycoprotein. The cDNA for FcγRIII encodes a predicted peptide of 233 residues (Mr 26 kDa) which, on polymorphonuclear neutrophils (PMNs), appears to be bound to the membrane through a phosphatidylinositol glycan (PIG) linkage (Selvaraj, P., et al. (1988) *Nature* 333:565–567; Simmons, D. and Seed, B. (1988) *Nature* 333:568–570). Several lines of evidence suggest that PMNs express a different form of FcγRIII than macrophages and natural killer (NK) cells. In addition to the differences between FcγRIII on granulocytes and NK cells, a structural polymorphism of this receptor on neutrophils has been demonstrated that may result from two allotypic forms of FcγRIII (Werner, G., et al. (1986) in

*Leukocyte Typing II* (vol. 3) (Reinherz E. L. et al. ed.) pp. 109–121 Springer Verlag).

The bispecific molecules of the invention have at least two distinct binding specificities. In one embodiment, the bispecific molecules of the invention have a binding specificity for a human lipoprotein, such as human low density lipoprotein (LDL) and a binding specificity for an Fc-receptor for immunoglobulin G (IgG) of a human effector cell. Alternatively, the bispecific molecules of the invention have a binding specificity for human high density lipoprotein (HDL) and a binding specificity for an Fc-receptor for immunoglobulin G (IgG) of a human effector cell.

In a preferred embodiment, bispecific molecules of the invention bind a human Fc receptor without being blocked by the binding of human IgG to the receptor. Since the FcγRI receptor binds monomeric IgG with high affinity, it is preferred that the receptor binding specificity is provided by a binding agent which binds to an epitope of the FcγRI receptor, which is distinct from the Fc (or ligand binding) site of the receptor. A preferred Fcγ receptor binding agent is an antibody, antibody fragment, antibody variable region, or genetic construct having the following characteristics: (a) the agent reacts specifically with human FcγRI receptor, FcγRII receptor or FcγRIII receptor; (b) the agent reacts with human FcγRI receptor, FcγRII receptor or FcγRIII receptor through the agent's antigen binding region and not its Fc portion; (c) the agent reacts with an epitope of human FcγRI receptor, FcγRII receptor or FcγRIII receptor which is distinct from the Fc binding (i.e., ligand binding) site of the receptor; and (d) the agent binds ligand (e.g., Fc)-occupied receptor.

The anti-Fcγ receptor antibodies of this invention can be produced as described in U.S. Pat. No. 4,954,617 (Fanger et al., "Monoclonal Antibodies to Fc Receptors for Immunoglobulin G on Human Mononuclear Phagocytes"), the contents of which are incorporated herein by reference.

The binding specificity for a human lipoprotein, such as human LDL can be provided by a binding agent which specifically binds an epitope of human LDL. Likewise, the binding specificity for human HDL can be provided by a binding agent which specifically binds an epitope of human HDL. Anti-LDL antibodies or LDL-binding fragments thereof or anti-HDL antibodies or HDL binding fragments thereof, can be used. These antibodies can be produced by conventional monoclonal antibody methodology, e.g., the standard somatic cell hybridization technique of Kohler et al. ((1975) *Nature* 256:495), using human LDL, or fragment thereof, or human HDL, or a fragment thereof, as the immunogen. A mammal, (e.g., a mouse, hamster, or rabbit) can be immunized with an immunogenic form of a human lipoprotein, such as human LDL or portion thereof, or human HDL or a portion thereof. Techniques for conferring immunogenicity on a protein or peptide include conjugation to carriers or other techniques well known in the art. For example, the protein or peptide can be administered in the presence of adjuvant. The progress of immunization can be monitored by detection of antibody titers in plasma or serum. Standard ELISA or other immunoassay can be used with the immunogen as antigen to assess the levels of antibodies.

Following immunization, antisera can be obtained and, if desired, polyclonal antibodies isolated from the sera. To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art. For example, the hybridoma technique originally developed by Kohler and Milstein ((1975) *Nature* 256:495–497) as well as other techniques such as the human B-cell hybridoma technique (Kozbar et al., (1983) *Immunol. Today* 4:72), the EBV-hybridoma technique to produce human monoclonal antibodies (Cole et al. Monoclonal Antibodies in Cancer Therapy (1985) (Allen R. Bliss, Inc., pages 77–96), and screening of combinatorial antibody libraries (Huse et al., (1989) *Science* 246:1275). Hybridoma cells can be screened immunochemically for production of antibodies specifically reactive with the peptide and monoclonal antibodies isolated.

The term antibody as used herein is intended to include fragments thereof which are also specifically reactive with an Fcγ receptor or a human lipoprotein as described herein. Antibodies can be fragmented using conventional techniques and the fragments screened for utility in the same manner as described above for whole antibodies. For example, F(ab')$_2$ fragments can be generated by treating antibody with pepsin. The resulting F(ab')$_2$ fragment can be treated to reduce disulfide bridges to produce Fab' fragments. The antibody of the present invention is further intended to include bispecific and chimeric molecules.

When antibodies produced in non-human subjects are used therapeutically in humans, they are recognized to varying degrees as foreign and an immune response may be generated in the patient. One approach for minimizing or eliminating this problem, which is preferable to general immunosuppression, is to produce chimeric antibody derivatives, i.e., antibody molecules that combine a non-human animal variable region and a human constant region. Chimeric antibody molecules can include, for example, the antigen binding domain from an antibody of a mouse, rat, or other species, with human constant regions. A variety of approaches for making chimeric antibodies have been described and can be used to make chimeric antibodies containing the immunoglobulin variable region of interest. See, for example, Morrison et al., (1985) *Proc. Natl. Acad. Sci. U.S.A.* 81:6851; Takeda et al., (1985) *Nature* 314:452, Cabilly et al., U.S. Pat. No. 4,816,567; Boss et al., U.S. Pat. No. 4,816,397; Tanaguchi et al., European Patent Publication EP 171496; European Patent Publication 0173494, United Kingdom Patent GB 2177096B. It is expected that such chimeric antibodies would be less immunogenic in a human subject than the corresponding non-chimeric antibody.

For human therapeutic purposes the monoclonal or chimeric antibodies specifically reactive with a human lipoprotein, such as human LDL, or a portion thereof, and human HDL or a portion thereof as described herein can be further humanized by producing human constant region chimeras, in which parts of the variable regions, especially the conserved framework regions of the antigen-binding domain, are of human origin and only the hypervariable regions are of non-human origin. Such altered immunoglobulin molecules may be made by any of several techniques known in the art, (e.g., Teng et al., (1983) *Proc. Natl. Acad. Sci. U.S.A.*, 80:7308–7312 ; Kozbor et al., (1983) *Immunology Today*, 4:7279; Olsson et al., (1982) *Meth. Enzymol.*, 92:3–16 ), and are preferably made according to the teachings of PCT Publication WO92/06193 or EP 0239400. Humanized antibodies can be commercially produced by, for example, Scotgen Limited, 2 Holly Road, Twickenham, Middlesex, Great Britain. Humanized antibodies which have reduced immunogenicity are preferred for immunotherapy in human subjects. Immunotherapy with a humanized antibody will likely reduce the necessity for any concomitant immunosuppression and may result in increased long term effectiveness for the treatment of chronic disease situations or situations requiring repeated antibody treatments.

Another method of generating specific antibodies, or antibody fragments, reactive against Fcγ receptors or human lipoproteins, such as human LDL, or a portion thereof, and human HDL, or a portion thereof, is to screen expression libraries encoding immunoglobulin genes, or portions thereof, expressed in bacteria with the Fcγ receptor or human lipoprotein, such as human LDL, or a portion thereof, and human HDL, or a portion thereof. For example, complete Fab fragments, VH regions and Fv regions can be expressed in bacteria using phage expression libraries. See for example Ward et al., *Nature*, 341: 544–546: (1989); Huse et al., (1989) *Science*, 246: 1275–1281; and McCafferty et al., (1990) *Nature*, 348: 552–554. Screening such libraries with, for example, a fragment of human LDL or human HDL can identify immunoglobin fragments reactive with human LDL or human HDL, respectively. Alternatively, the SCID-hu mouse developed by Genpharm can be used to produce antibodies, or fragments thereof.

The human LDL or human HDL can be purified or partially purified from serum, or produced by chemical synthesis or recombinant technique. Human LDL or human HDL, can be purified from serum, chemical precursors or cellular material by techniques known in the art including ion-exchange chromatography, gel filtration chromatography, electrophoresis or immunopurification using an antibody specific for human LDL or portion thereof or an antibody specific for human HDL or a portion thereof. It will be appreciated that fragments of human LDL or human HDL can also be employed as the component to which a binding specificity is provided. A preferred anti-LDL monoclonal antibody is A01609, which is a high affinity IgG1 (Ka=$5 \times 10^{10}$/mol) antibody that recognizes an epitope on human apoprotein B, with no cross-reactivity to apoprotein A-I or A-II (Medix Biotech, Inc., Foster City, Calif.). Several hybridomas that produce anti-human HDL monoclonal antibodies can be obtained from American Type Culture Collection, Rockville, Md. The hybridoma HA62 HA227A2.7D3 (ATCC HB 8741), the generation of which is described in U.S. Pat. No. 4,677,057, the contents of which are incorporated herein by reference, produces mouse anti-human apolipoprotein A (apo-A-I) monoclonal antibodies. The hybridoma HA61 H112F3.1A11 (ATCC HB 8743), the generation of which is described in U.S. Pat. No. 4,677,057, produces mouse anti-human apolipoprotein A (apo-A-II) monoclonal antibodies. The hybridoma 611 AV63C2.1F1 (ATCC HB 8744), the generation of which is also described in U.S. Pat. No. 4,677,057, produces mouse anti-human apolipoprotein A (apo-A-I) monoclonal antibodies. The hybridoma HA60 HA22GF.5F8 (ATCC 8745), the generation of which is described in U.S. Pat. No. 4,677,057, produces mouse anti-human apolipoprotein A (apo-A-I) monoclonal antibodies.

Preferred bispecific molecules of the invention are bispecific antibodies, heteroantibodies and single-chain bispecific polypeptides. Bispecific antibodies resemble single antibodies (or antibody fragments) which have two different antigen binding regions (variable regions). Bispecific antibodies of this invention have one binding region for a human Fcγ receptor (i.e., FcγRI, FcγRII, FcγRIII) and one binding region for an epitope of a human lipoprotein, such as human LDL or human HDL. Bispecific antibodies can be produced by chemical techniques (see e.g., Kranz et al. *Proc. Natl. Acad. Sci. USA* 78:5807 (1981)), by "polydoma" techniques (see U.S. Pat. No. 4,474,893, issued to Reading), or by recombinant DNA techniques.

Heteroantibodies are two or more antibodies, or antibody binding fragments (Fab) linked together, each antibody or fragment having a different binding specificity. Heteroantibodies of the invention comprise an antibody (or antigen binding fragment) specific for a human Fcγ receptor (i.e., FcγRI, FcγRII, FcγRIII), coupled to an antibody (or antigen binding fragment) specific for an epitope of a human lipoprotein, such as human LDL or human HDL. Heteroantibodies can be prepared by conjugating an Fcγ receptor antibody with an antibody specific for an epitope of either human LDL or human HDL. A variety of coupling or crosslinking agents can be used to conjugate the antibodies including protein A, carbodiimide, dimaleimide, dithio-bis-nitrobenzoic acid (DTNB), N-succinimidyl-S acetyl-thioacetate (SATA), and N-succinimidyl-3-(2-pyridyldithio) propionate (SPDP). SATA, DTNB and SPDP are preferred coupling agents. Procedures for crosslinking antibodies with these agents are well-known in the art. See e.g., Pierce ImmunoTechnology Catalog & Handbook (1991) E8-E39, Karpovsky et al. (1984) *J. Exp. Med.* 160:1686; Liu et al. (1985) *Proc. Natl. Acad. Sci. USA* 82:8648; Segal e al., U.S. Pat. No. 4,676,980 (Jun. 30, 1987); and Brennan, (1986) Biotech. 4:424.

Bispecific molecules of this invention can be prepared by conjugating a gene encoding a binding specificity for either human LDL (i.e., an epitope of human LDL) or human HDL (i.e., an epitope of human HDL) to a gene encoding at least the binding region of an antibody chain which recognizes a human Fcγ receptor (i.e., FcγRI, FcγRII, FcγRIII). This construct is transfected into a host cell (such as a myeloma) which constitutively expresses the corresponding heavy or light chain, thereby enabling the reconstitution of a bispecific, single-chain antibody, two-chain antibody (or single chain or two-chain fragment thereof such as Fab) having a binding specificity for human LDL and for a human FcγR. Construction and cloning of such a gene construct can be performed by standard procedures.

The function of human Fcγ receptors is dictated in part by the type of effector cell on which they are displayed. Effector cells which can be targeted by the bispecific molecules of the invention include monocytes, macrophages, leukocytes, activated neutrophils, activated natural killer (NK) cells, tissue macrophages, platelets and eosinophils. Of particular interest as targets due to their role in the pathogenesis of atherosclerosis are human monocytes and macrophages which are capable of developing into foam cells (i.e., cholesteryl ester-laden white blood cells) which are a major constituent of atheromatous lesions.

Many factors influence the number of receptors expressed and detected on effector cells. For example, cell culture conditions, the presence or absence of human IgG which may interfere with measurement, natural cytokines to which the cells were exposed in vivo, and hormones and cytokines in cell culture medium may influence receptor expression. FcγRI expression is almost exclusively restricted to mononuclear phagocytes whereas FcγRII is expressed on the surface of virtually all hematopoietic cells except erythrocytes and is probably the sole FcγR on human platelets (Rosenfeld, S. I., et al. (1985) *J. Clin. Invest.* 76:2317–2322). FcγRIII is widely recognized for its high level of expression (100,000–200,000 sites per cell) on human neutrophils (Fleit, H. B., et al. (1982) *Proc. Natl. Acad. Sci. USA* 79:3275–3279; Petroni, K. C., et al. (1988) *J. Immunol.* 140:3467–3472).

Myeloid cells, with the exception of eosinophils, when exposed to interferon γ (IFN-γ) have been shown to increase expression of FcγRI and increase killing of red blood cells via FcγRI, FcγRII and FcγRIII (see e.g., Fanger, M. W., et al. (1989) *Immunol. Today* 10:92–99). Effector cells can also be activated by other cytokines such as tumor necrosis factor (TNF), granulocyte colony-stimulating factor (G-CSF), granulocyte-macrophage colony-stimulating factor (GM-CSF), lymphotoxin, interleukin-2 (IL-2) and interleukin-3 (IL-3).

As therapeutic agents, bispecific molecules of this invention can be administered to an individual to target human LDL for phagocytosis and subsequent degradation by an effector cell, such as a human monocyte or macrophage. To influence lipoprotein metabolism in vivo, the bispecific molecules can be targeted to an Fcγ receptor which is not involved in macrophage foam cell development during atherogenesis. For example, a therapeutic amount of a heteroantibody comprising a first antibody or antigen-binding fragment thereof which immunologically binds human LDL, and a second antibody or antigen-binding fragment thereof which immunologically binds an Fcγ receptor can be administered to an individual in the form of a physiologically acceptable solution. The heteroantibody will target LDL to the Fcγ receptor on the monocyte or macrophage to result in LDL uptake and metabolism such that cholesteryl ester accumulation is reduced.

HDL is known to play a role in cholesterol efflux from extrahepatic tissues, such as vascular tissue, to the liver where it can be metabolized. See, e.g., Badimon, J. J. et al. (1992) *Circulation* (Supp. III) 86(6):III-86-III-94; Castell, W. P. et al (1977) *Circulation* 55(5):767–772. Moreover, it has been shown that plasma HDL both inhibits the development of experimental atherosclerosis and induces regression of the lipid infiltration into vessel (e.g., aortic) walls. Badimon, J. J. et al., supra. Therefore, bispecific molecules of the present invention can also be administered to an individual to target human HDL to effector cells, such as macrophage-derived foam cells, to take up and/or remove cholesterol or other harmful lipids from the effector cell. For example, a therapeutic amount of a heteroantibody comprising a first antibody or antigen-binding fragment thereof which immunologically binds human HDL, and a second antibody or antigen-binding fragment thereof which immunologically binds an Fcγ receptor can be administered to an individual in the form of a physiologically acceptable solution. The heteroantibody will target HDL to the Fcγ receptor on the monocyte or macrophage, e.g, a macrophage-derived foam cell, to result in HI)L uptake and/or removal of cholesterol from the monocyte or macrophage.

Alternatively, effector cells from the individual can be obtained from the host to be treated or any other immunologically compatible donor and cultured in vitro with bispecific molecules to produce opsonized effector cells having attached bispecific molecules. The opsonized effector cells can be administered as a suspension of cells in a physiologically acceptable solution. The number of cells administered can be in the order of $10^8$–$10^9$, but will vary depending on the therapeutic purpose. Opsonized effector cells or bispecific molecules can be administered to an individual intravenously, intramuscularly, or intraperitoneally at dosages and for lengths of time known in the art, (see e.g., Ball, E. D., et al. *J. Hematotherapy* (1992) in press; de Leij, L., et al. (Oct. 9–13, 1990) Second International Conference, Seillac, France, *Bispecific Antibodies and Targeted Cellular Cytotoxicity*, pp. 249–253; Clark, M., et al. (Oct. 9–13, 1990) Second International Conference, Seillac, France, *Bispecific Antibodies and Targeted Cellular Cytotoxicity*, pp. 243–247; and Nitta, T. et al. (Feb. 17, 1990) The Lancet 335:368–371).

The bispecific molecules of this invention are particularly well suited for in vivo therapy even when a large excess of human IgG is present in vivo ("antibody blockade"). The anti-FcγR component of the bispecific molecules bind epitopes of the appropriate FcγR distinct from the ligand IgG binding domain which are not blocked by endogenous IgG. Thus, IgG binding to the receptor does not interfere with binding of the bispecific molecule to an effector cell or interfere with functioning of effector cells.

The bispecific molecules of the invention can also be used in diagnostic applications. Recent studies indicate that LDL immune complexes consisting of anti-LDL antibodies bound to human LDL may contribute to macrophage foam cell development by uptake through IgG Fc receptors and/or macrophage scavenger receptors. As human mononuclear phagocytes possess all three classes of IgG Fc receptors, FcγRI, FcγRII and FcγRIII, the effects of LDL immune complexes can be determined with respect to each type of receptor. Bispecific molecules of the invention comprising an anti-Fcγ receptor antibody linked to an anti-LDL antibody can be used to target a specific Fcγ receptor to determine which receptors may be involved in the development of cholesteryl ester-laden foam cells during atherogenesis. Fcγ receptors involved in macrophage foam cell development can be interfered with, blocked or down-regulated to reduce the formation of atheromatous lesions. For example, as shown in Example 7, an anti-Fcγ receptor antibody can be used to block binding of the receptor. More particularly, it was shown in Example 7 that targeting LDL to FcγRI with a bispecific molecule results in decreased lipid retention by monocytes, as determined by, for example, the technique of Araki et al. ((1990) *Analytical Biochemistry* 185:339–345). Fcγ receptors which are not involved in foam cell development can be targeted with bispecific molecules of the invention to facilitate macrophage phagocytosis and degradation of LDL.

Bispecific molecules of the present invention comprising, for example, an anti-Fcγ receptor antibody linked to an anti-HDL antibody can be used to target HDL to effector cells isolated from an individual to determine the capacity of the HDL to take up cholesterol or other harmful lipids from that individual's effector cells. This diagnostic application of the present invention can be used to predict the ability of HDL to reduce the cholesterol content of an individual's effector cells, thereby establishing the feasibility of treating the individual, e.g, an individual with atherosclerosis, with a bispecific molecule which targets HDL to Fcγ receptors of the individual. The lipid content of the individual's effector cells prior to and after targeting, via the bispecific molecules of the present invention, HDL thereto can be measured using standard techniques, such as those described below in Example 7.

To diagnose an individual's risk of developing atherosclerosis, white blood cells, such as monocytes or macrophages can be obtained from the individual and contacted with bispecific molecules of the invention and LDL, or LDL immune complexes under conditions appropriate for binding of the bispecific molecule to the Fcγ receptor and LDL or LDL immune complexes. The level of cholesteryl ester accumulated by the cell can be determined by, for example, the method of Araki et al. (supra), as indicative of the tendency of the cell to develop into a foam cell and identifies the individual as at risk of developing atherosclerosis in the context of immune complex stimulation. Such a determination may also indicate the tendency of the cell to metabolize LDL and accumulate cholesteryl ester via other pathways, such as those associated with scavenger receptors.

The following examples describe the effects of bispecific LDL immune complexes directed to Fcγ receptor types 1, II, and III on monocytes in comparison to the effects of similarly prepared bispecific complexes that targeted LDL to HLA Class I antigens. Each type of bispecific molecule was effective in targeting $^{125}$I-LDL to its respective site on the cell surface. Using fluorophore-labeled LDL and flow cytometry, bispecific complexes directed to Fcγ receptor types I or II, but not to LILA Class I antigens, caused a two to seven-fold increase in cell-associated fluorescence relative to control cells treated with LDL in the absence of heteroantibody. Using $^{125}$1-labeled complexes, metabolic degradation of LDL was demonstrated in association with each of the three types of Fcγ receptors.

The present invention is further illustrated by the following examples which in no way should be construed as being further limiting. The contents of all cited references (including literature references, issued patents, published patent applications, and co-pending patent applications) cited throughout this application are hereby expressly incorporated by reference.

EXAMPLES

MATERIALS AND METHODS

Chemicals and Reagents

SATA and SPDP, (N-succinimidyl-S-acetylthioacetate and N-succinimidyl-3-[2-pyridyldithio]propionate, respectively), dimethylformamide, and hydroxylamine were obtained from Pierce, Rockford, Ill. Unless otherwise indicated, all other reagents were obtained locally or from Sigma Chemical Co., St. Louis, Mo.

Monoclonal Antibodies (mAb)

All mAb used were of murine origin. Purified anti-FcγRI (mAb 22, an IgG1), anti-FcγRII (mAb IV.3, an IgG2b), and anti-FcγRIII (mAb 3G8, an IgG1) were obtained from Medarex, Inc., W. Lebanon, N.H. Anti-LDL mAb A01609 is a high affinity IgG1($K_a$=5×10$^{10}$/mol) that recognizes an epitope on human apoprotein B, with no cross-reactivity to apo A-I or A-II and was obtained from Medix Biotech, Inc., Foster City, Calif. This mAb reacted to adsorbed native LDL by ELISA, at 4° C. and 37° C., under conditions that inhibit oxidation (Palinski, W., et al. (1990) *Arteriosclerosis* 10:325–335). Anti-HLA Class I (mAb BBM. 1, an IgG2b), that recognizes an epitope on β2-microglobulin (Brodsky, F. M., et al. (1 979) *Eur. J. Immunol.* 9:536–545), was obtained from American Type Culture Collection, Rockville, Md.

Production of Bispecific Antibodies

Unless otherwise indicated, all steps were carried out at room temperature. Intact mAb were used for all conjugations except for preparation of anti-FcγRIIIxanti-LDL, which was done with F(ab')$_2$ fragments. Prior to derivatization, each mAb was dialyzed into Ca$^2$+, and Mg$^2$+-free phosphate-buffered saline (PBS), pH 7.5, containing 1.25 mM EDTA and used at approximately 2–6 mg/ml. Heteroantibodies were prepared by first reacting, anti-myeloid cell mAb with the heterobifunctional crosslinker SPDP (Karpovsky, B., et al. (1984) *J. Exp. Med.* 160:1686–1701), and anti-LDL mAb with SATA (Duncan, R. J. S., et al. (1983) *Anal. Biochem.* 132:68–73). To prepare SPDP-labeled mAb (anti-FcγR or anti-HLA class 1), SPDP was added to mAb at an 8:1 molar ratio (from an SPDP stock solution of 3.2 mg/ml freshly prepared in ethanol) for one hour under N$_2$. SATA-anti-LDL was prepared by adding SATA to anti-LDL mAb at a 12:1 molar ratio (freshly prepared in dimethylformamide, 2% v/v added to mAb) for one hour also under N$_2$. Both preparations were dialyzed overnight into 50 mM sodium phosphate plus 5 mM EDTA, pH 7.5, at 4° C. The next day SPDP-mAb and SATA-anti-LDL were combined at a 2:1 molar ratio respectively, and coupling was initiated by addition of freshly-prepared hydroxylamine (added from a 0.5M 10X stock) in 50 mM sodium phosphate plus EDTA, pH 7.5. Coupling was allowed to continue overnight at room temperature under N$_2$. After coupling, the heteroantibodies were separated from unreacted monomers by HPLC on TSK-250 or GPC 300 analytical sizing columns (SynChron, Inc., Lafayette, Ind.) equilibrated in endotoxin-free PBS. Pooled fractions were subsequently rechecked by HPLC to verify the absence of IgG monomers. With this protocol, approximately 50% of the total protein typically is recovered as heteroantibody. All fractions were sterilized by passage through a 0.2 μm filter, and stored at 4° C. Protein content was determined by BCA assay (Picrce) and by determination of optical density (A$_{280}$) using an IgG extinction coefficient of 1.43 OD/mg/ml.

Lipoproteins

LDL (d>1.019<1.063 g/ml) was isolated from the serum of fasted donors by ultracentrifugation according to standard techniques (Goldstein, J. L., et al. (1983) *Methods in Enzymology* 98:241–260). A cocktail of freshly prepared protease inhibitors (Cadigan, K. M., et al. (1988) *J. Biol. Chem.* 263:274–282) in addition to EDTA was added to the blood at the outset. Following isolation, LDL was dialyzed extensively into buffer containing, 10 mM sodium phosphate, 1.2 mM EDTA, and 140 mM NaCl, pH 7.4, prepared in sterile pyrogen-free water. Final storage was in the presence of 25 μg/ml gentamicin under N$_2$ (Lopes-Virella, M. F., et al., supra). Protein content was determined by a modified Lowry assay using bovine serum albumin (BSA) as the standard (Peterson, G. L. A. Anal. Biochem. 83:346–356). LDL was labeled with $^{125}$I according to the McFarlane method as described (Goldstein, J. L., et al., supra). The specific activity of all preparations ranged from 220–440 CPM per ng protein, and all preparations were used within three weeks. BODIPY-LDL (LDL*) and BODIPY-acetyl-LDL (AcLDL*), conjugates with excitation and emission spectra similar to that of fluorescein, were obtained from Molecular Probes, Inc., Eugene, OR and used within three weeks of delivery. AcLDL was prepared by the method of Basu et al. (Basu, S. K., et al. (1976) *Proc. Natl. Acad. Sci. USA* 73:3178–3182); in preliminary experiments all AcLDL preparations caused greater than 80% inhibition of uptake of ACLDL* by monocytes at 37° C.; likewise, all LDI, preparations caused geater than 80% inhibition of uptake of LDL*. Lipoprotein deficient serum was prepared from bovine calf serum by ultracentrifugation according to standard techniques (Goldstein, J. L., et al., supra). It was adjusted to 5 mg/ml protein with saline, sterilized by passage through a 0.2 μm filter, and used in RPMI 1640 at 10%.

Preparation of Leukocytes

Freshly isolated monocytes or polymorphonuclear (PMN) were used in all experiments. Monocytes were obtained from leukapheresis packs of normal donors as described previously (Shen, L., et al. (1986) *Clin. Exp. Immunol.* 65:387–395). Platelets were removed by three washes in Versene buffer (Sporn, S. A., et al. (1990) *J. Immunol.* 144:4434–4441) (Gibco, Grand Island, N.Y.), and final preparations typically were geater than 90% monocytes as judged by morphology. In all experiments, cells were washed extensively in RPMI 1640 (JRH Biologicals, Inc., Lenexa, Kans.) containing 2 mg/ml BSA, 15 mM HEPES, and 25 μg/ml gentamicin (monocyte culture medium), and resuspended in RPMI 1640 plus 10% FCS and gentamicin unless otherwise indicated. PMN were separated from whole venous blood of normal donors by the discontinuous Percoll gradient procedure (Haslett, C., et al. (1985) *Am. J. Pathol.* 119:101 –110). Final suspensions were in RPMI 1640 plus 10% FCS and gentamicin unless otherwise indicated. Viability, as assessed by exclusion of ethidium bromide (Mishell, B. B. and Shiigi, S. M. (1980) *Selected Methods in Immunology*, pp. 21–22), was always greater than 95% for both monocytes and PMN.

1251-LDL Binding Assay

Binding of $^{125}$I-LDL to monocytes in the presence and absence of heteroantibodies was done on ice in a two step procedure. $1\times10^6$ monocytes in RPMI 1640 plus 10% LPDS were added to eppendorf tubes containing saturating amounts of heteroantibodies for I hour on ice. In specificity experiments, binding of heteroantibodies was done in the presence of 0.5 mg/ml of the corresponding unconjugated anti-FcγR or anti-HLA Class I antibodies. After binding, the cells were washed twice in one ml of ice cold 10% LPDS, and then received a saturating amount of $^{125}$I-LDL (100 mg/ml) in 10% LPDS, also for one hour on ice. In some experiments, the latter step was also done in the presence of 2 mg/ml of unlabeled LDL, as a control for LDL specificity. The cells were then washed once in ice cold PBS containing 2 mg/mi of BSA, followed by two washes in PBS containing no BSA. Suspensions of cells were pelleted through 200 μl of 170,000 kDa dextran in PBS in a microfuge, and cell pellets were cut from the tubes and counted in a gamma counter. Some pellets were lysed in 0.1 N NaOH for determination of total cell protein by modified Lowry assay (Peterson, G. L. A., supra). Results are expressed as ng $^{125}$I-LDL bound per mg cell protein.

Uptake of Bispecific LDL Immune Complexes

All experiments were done under sterile conditions. For each experiment, bispecific LDL immune complexes (bispecific LDL*-IC) were freshly prepared by combining 4 μg/ml of LDL* with heteroantibodies in eppendorf tubes in monocyte culture medium (without serum or unlabeled LDL unless otherwise indicated), and incubating for one hour at room temperature, prior to adding cells in RPMI 1640 plus 10% FCS. That concentration of LDL* was chosen because it gave a satisfactory signal to noise ratio. In all experiments, a control consisting of LDL* alone was set up by substituting medium for heteroantibody. The final volume of bispecific complexes prior to addition of cells was 50 ml; 100 ml of cells at $1\times10^7$/ml were added for a final volume of 150 ml. The tubes were then mixed by gentle pipetting, and incubated at 4° C. or 37° C. as indicated. Final mAb or heteroantibody concentrations are shown in each figure; the final concentration of LDL* in all preparations was 1.33 μg/ml unless otherwise indicated. Blocking studies with unlabeled LDL or unlabeled AcLDL were done by pretreating cells with an excess amount of lipoprotein for one hour at room temperature, and then adding them to bispecific complexes without washout.

Analysis of Cell-associated Fluorescence of LDL* and AcLDL*

In all experiments, cells were removed after various times of incubation and washed twice with one ml of PBS at room temperature. The final suspension was in cold 1% methanol-free paraformaldehyde (Eastman-Kodak, Rochester, N.Y.) in PBS. For cytofluorogaphic analysis, samples were analyzed for green fluorescence on a FACScan (Becton-Dickinson). The excitation wavelength was 488 nm and emission at 515 nm was analyzed. Monocyte or PMN were rated on the basis of blue forward vs. right angle light scatter. In most experiments, the gain for linear fluorescence was set such that the LDL*-alone or AcLDL*-alone control had a mean fluorescence intensity of approximately 100 on a scale of 1000; for cells treated with LDL*-alone a second region was also set arbitrarily such that 5% of the total population was positive for green fluorescence.

LDL Degradation Assay

The degradation of bispecific LDL-IC following uptake through FcγR was assessed by a standard type assay of acid-soluble products that did not contain free iodide (Goldstein, J. L. et al., supra). All treatments were corrected for background degradation by including cell-free controls, with and without antibody. For these studies monocytes were treated with and without saturating amounts of heteroantibody for one hour on ice; all tubes then received 100 μg/ml of $^{125}$I-LDL in 10% LPDS. The cells and cell-free controls were incubated for 4 hours at 37°, after which cell supernatants werc harvested and analyzed for acid-soluble products (Goldstein, J. L., et al., supra). Cell pellets were immediately chilled on ice, washed, spun through dextran and counted in a gamma counter as described above. In some experiments, parallel sets of cells were kept on ice and processed for determination of cell-bound radioactivity as described above. In all experiments cell pellets were lysed in 0.1 N NAOH for determination of total protein by modified Lowry assay (Peterson, G. L. A., supra). Results from degradation assays are expressed as ng $^{125}$I-LDL degraded per mg cell protein per four hours incubation at 37° C.

Statistics

Groups of data from three degradation assays were compared by one-way analysis of variance, and multiple comparisons were made with the Neuman-Keuls test. P values= to 0.05 were taken to indicate significance (Zar, J. H. (1974) *Biostatistical Analvsis*, pp. 185–191).

Example 1

Binding of 1251-LDL to Cells Mediated Through FcγR

Figure 1B:
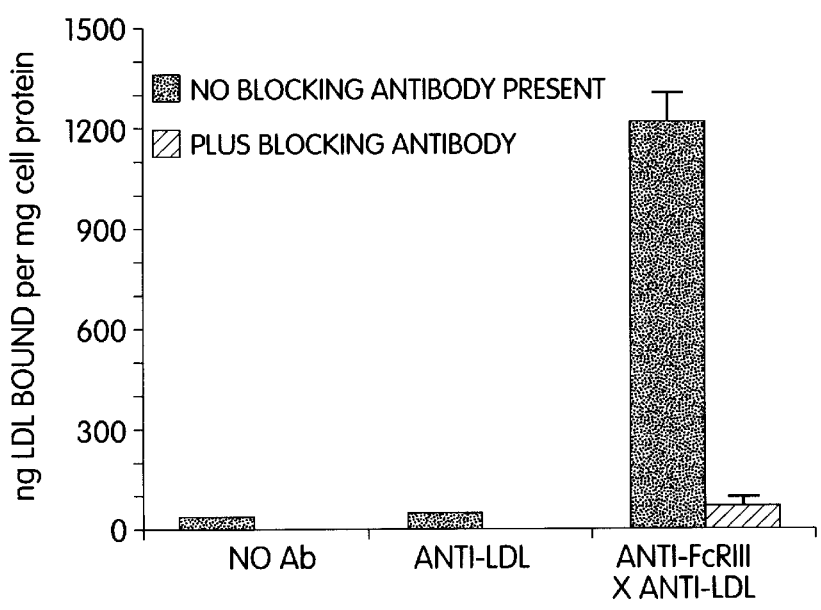

To determine the capacity and specificity of heteroantibodies to deliver LDL to cells via FcγR, monocytes on ice were treated with 100 μg/ml of $^{125}$I-LDL plus saturating amounts of the heteroantibodies anti-FcγRI×anti-LDL, anti-FcγRII×anti-LDL, or anti-HLA Class I×anti-LDL as described in "Methods". PMN were used to test anti-FcγRIII×anti-LDL, since they express much greater amounts of FcγRIII than monocytes. The amount of $^{125}$I-LDL used was also determined to be saturating. In all experiments, controls were done consisting of $^{125}$I-LDL alone and $^{125}$I-LDL plus anti-LDL. For controls of FcγR specificity, the binding of $^{125}$I-LDL in parallel experiments was done in the presence of excess amounts of the corresponding anti-FcγR mAb. For controls of LDL specificity, in some experiments the binding of $^{125}$I-LDL to cells treated with bispecific antibodies was done in presence of excess (1 mg/ml) unlabeled LDL. A typical experiment is shown in FIG. 1. For monocytes (FIG. 1A), relative to no antibody and anti-LDL antibody controls: anti-FcγRI×anti-LDL bound five times as much $^{125}$I-LDL; anti-FcγRII×anti-LDL bound twenty times as much $^{125}$I-LDL; and anti-HLA Class I×anti-LDL bound eight times as much $^{125}$I-LDL. The unconjugated anti-LDL bound no $^{125}$I-LDL to cells because murine IgG1 mAb do not bind with high affinity to any type of human FcγR (Looney, R. J., et al. (1986) *J. Immunol.* 136:1641–1647; Lubeck, M. D., et al. (1985) *J. Immunol.* 135:1299–1304). Using PMN (FIG. 1B), the amount of anti-FcγRIII×anti-LDL bound was twenty times the controls. When binding of heteroantibodies was done in the presence of an excess amount of the corresponding anti- FcγR or anti-HLA Class I mAb, the subsequent binding of $^{125}$I-LDL was reduced to control levels (hatched bars). As was also expected, binding of 125I-LDL to cells labeled with heteroantibodies was totally inhibited in the presence of excess unlabeled LDL.

Example 2

Effects of Bispecific LDL*-IC

Figure 2A:
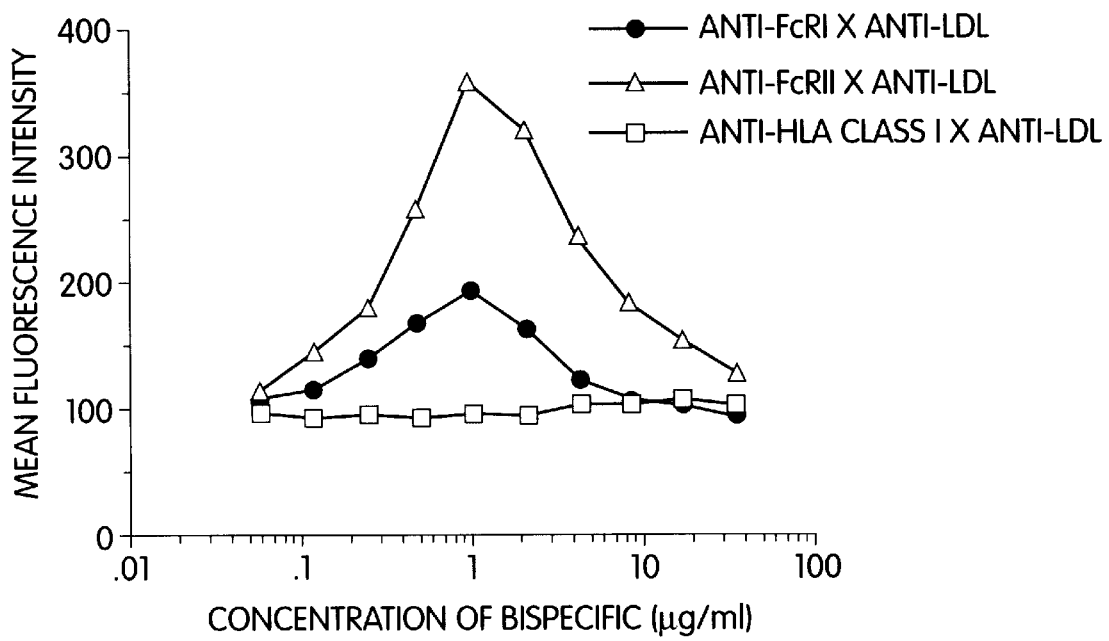
FIGS. 2A and 2B are graphic representations of the effects of bispecific LDL immune complexes (LDL*-IC) on myeloid cells. Monocytes (A) in 10% fetal calf serum (FCS) were treated with 4 μg/ml BODIPY-LDL plus varying amounts of anti-FcγRI×anti-LDL (circles), anti-FcγRII× anti-LDL (triangles), or anti-HLA Class I×anti-LDL (squares), for 2 hours and analyzed by flow cytometry as described in the examples. In (B), monocytes were treated similarly with BODIPY-LDL plus anti-FcγRII×anti-LDL at 4° C. (triangles) and 37° C. (circles). Shown in FIG. 2B are the means±SD of triplicate measurements of cell-associated LDL*.
Figure 2B:
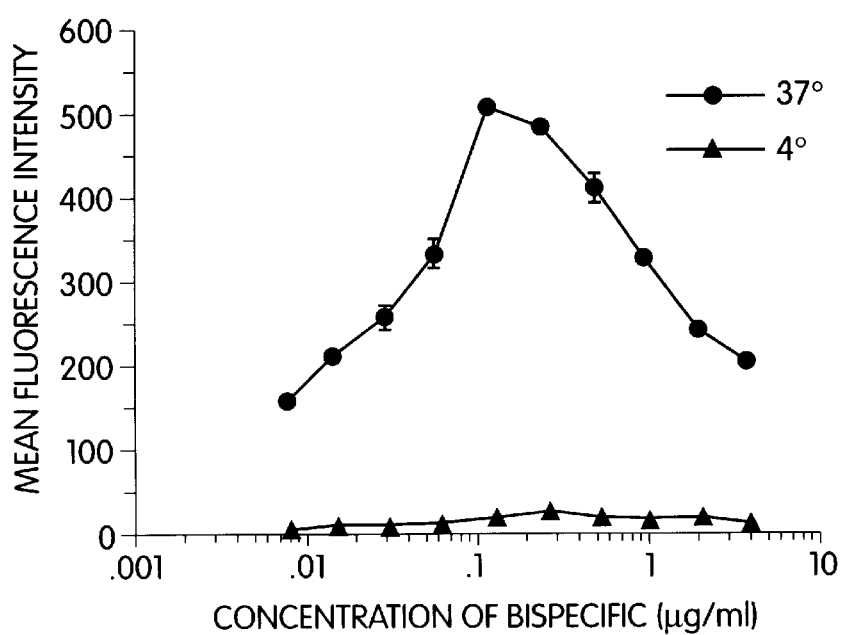

A typical experiment of the effects of bispecific LDL*-IC on monocytes is shown in FIG. 2. Monocyte were treated with preformed bispecific LDL*-IC (see "Methods"), prepared by preincubating BODIPY-LDL with varying amounts of bispecific anti-FcγRIxanti-LDL, anti-FcγRIIxanti-LDL, and as a non-FcγR control, anti-HLA Class Ixanti-LDL. The uptake of LDL* in the absence and presence of unconjugated anti-LDL was minimal and equal to that mediated by anti-HLA Class Ixanti-LDL, and did not change with increasing concentrations of antibody or heteroantibody, respectively (FIG. 2A). This occurred despite the fact that the anti-HLA Class I bispecific was effective in delivering LDL to cells (FIG. 1A). However, treatment with bispecific LDL*-IC prepared with anti-FcγRIxanti-LDL or anti-FcγRIIxanti-LDL resulted in an approximately 2- and 3.5-fold higher level respectively, of cell-associated LDL* compared with controls. Moreover, the highest level of cell-associated LDL* peaked at 1 μg/ml of heteroantibody. Relative to the LDL* alone control, more than 90% of the cells were fluorescent, and the distribution of fluorescence was unimodal. For several similar experiments the response to bispecific LDL*-IC relative to LDL-alone controls was usually two-fold for anti-FcγRIxanti-LDL, and three to seven-fold for anti-FcγRIIxanti-LDL. The inability of the anti-HLA Class Ixanti-LDL to mediate uptake of LDL* suggests that myeloid cell FcγR may interact uniquely with bispecific LDL*-IC and is consistent with previous studies showing that FcγR were the only phagocytic or cytotoxic trigger molecules on myeloid cells (Fanger, M. W., et al. (1989) *Immunology Today* 10:92–99). Unconjugated anti-LDL did not cause uptake of LDL* because as stated above, murine IgG1 mAb do not bind with high affinity to any type of FcγR (Looney, R. J., et al., supra; Lubeck, M. D)., et al., supra). The precipitin curve-like nature of the response to bispecific LDL*-IC is consistent with the interpretation that these molecules are reacting with multiple epitopes on the LDL molecules that enhance the ability of the complexes to bind and trigger metabolic uptake. Similar results with such molecules have also been reported in other systems (Taylor, R. P., et al. (1991) *Proc. Natl. Acad. Sci. USA* 88:3305–3309). For experiments described below where the amount of heteroantibody was not varied, the concentration of heteroantibody used was taken from the peaks of curves shown in FIG. 2.

Example 3

Effects of Temperature on the Response to Bispecific LDL*-IC

In order to establish that bispecific LDL*-IC were undergoing metabolic uptake by monocytes, we studied the effects of temperature on this phenomenon. In a typical experiment monocytes (FIG. 2B) were treated for 18 hours with bispecific LDL*-IC prepared with anti-FcγRIIxanti-LDL at both 4° C. and 37° C. Cell-associated fluorescence of LDL*-IC bound at 4° C. was low, relative to the total amount that had accumulated at 37° C. Despite the fact that bispecific LDL*-IC binds significantly to cells in the cold (FIG. 1), there was little change in cell-associated LDL* with time of incubation at 4° C. At 37° C. however, the accumulation of LDL*-IC was 4.4-times that of LDL*-alone. As phagocytic processes are inhibited at 4° C. (see kinetic and degradation studies below), these data are consistent with the interpretation that at 37° C. bispecific LDL*-IC were undergoing metabolic uptake. Also, since the effects of bispecific LDL*-IC at 4° C. or 37° C. are completely inhibited in the presence of excess anti-FcγR mAb (FIG. 1), it is likely that uptake occurs through specific FcγR and not through nonspecific pinocytotic pathways.

Example 4

Kinetic Studies

Figure 3:
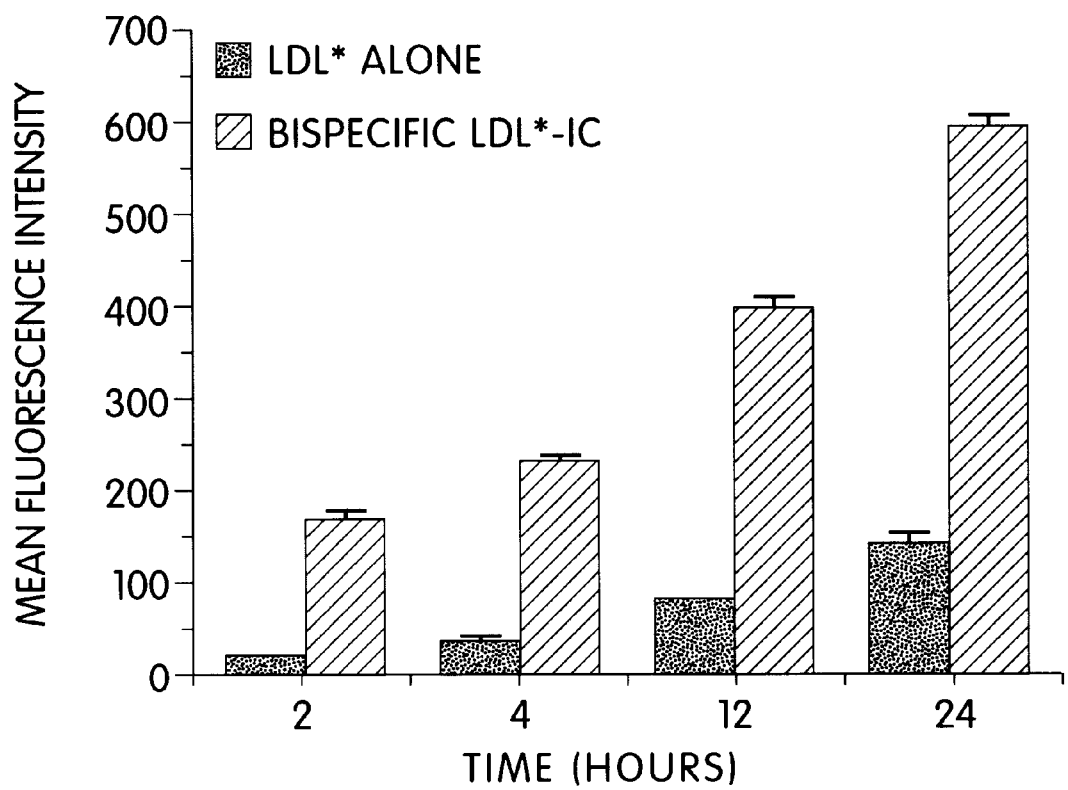
FIG. 3 is a graphic representation of the accumulation of bispecific LDL*-IC with time of culture at 37° C. Monocytes in 10% FCS were treated at 37° C. for the indicated times with BODIPY-LDL alone or bispecific LDL*-IC consisting of 0.5 μg/ml of anti-FcγRII×anti-LDL plus 1.33 μg/ml of BODIPY-LDL as described in the examples. Cell-associated fluorescence was analyzed by flow cytometry. Shown are the means±SD of triplicate measurements of cell-associated fluorescence.

To test whether the kinetics of the response to bispecific LDL*-IC were consistent with metabolic uptake, monocytes were treated with bispecific LDL*-IC prepared with anti-FcγRIIxanti-LDL for 2, 4, 12 and 24 hours at 37° C. As shown in FIG. 3, significant amounts of cell-associated LDL* were present after 2 hours of treatment with bispecific LDL*-IC and this continued to increase up to 24 hours. By 24 hours of treatment, the increase relative to cells treated with LDL*-alone was 4.3-fold, consistent with the studies discussed above. The same results were obtained in two other studies. As binding of bispecific LDL*-IC to cells is complete within one hour, the cumulative nature of the response to bispecific LDL*-IC is consistent with metabolic uptake.

Example 5

Effects of Excess LDL and AcLDL on the Response to Bispecific LDL*-IC

Several experiments were done with monocytes in order to determine if native LDL or scavenger receptors (Fogelman, A. M., et al. (1981) *J. Lipid. Res.* 22:1131–1 141; Knight, B. L. and Soutar, A. K. (1982) *Eur. J. Biochem.* 125:407–413) were involved in the uptake of bispecific LDL*-IC. In preliminary experiments, preparations of unlabeled LDL or AcLDL were checked for their ability to inhibit uptake of saturating amounts of their BODIPY-conjugates by monocytes at 37° C. LDL at 400 μg/ml, and AcLDL at 75 μg/ml caused greater than 80% inhibition of uptake of their respective BODIPY-conjugates. Thus, those concentrations were used to test for inhibition of uptake of bispecific LDL*-IC by monocytes at 37° C. In a typical experiment (Table 1), pretreatment of monocytes with LDL did not inhibit the uptake of bispecific LDL-IC (8.4 times LDL* alone), nor did pretreatment with unlabeled AcLDL (6.2 times LDL* alone). Thus a significant response to bispecific LDL*-IC occurred when LDL receptors were blocked with LDL, or when scavenger receptors were blocked with AcLDL. Consistent with the absence of a role for scavenger receptors is the fact that the antioxidant butylated hydroxytoluene (BHT) or superoxide dismutase had no effect on the response to bispecific LDL*-IC.

TABLE I

Uptake of LDL* or bispecific LDL*-IC in the presence of unlabeled LDL or unlabeled AcLDL.

| Condition | Cell-associated fluorescence of LDL* or AcLDL |
|---|---|
| LDL* plus LDL | 25 ± 2 |
| LDL*-IC plus LDL | 209 ± 5 |
| LDL* plus AcLDL | 51 + 2 |
| LDL*-IC plus AcLDL | 315 ± 3 |

Monocytes in serum-free medium were treated for 20 hours with LDL* alone or bispecific LDL*-IC consisting of 0.5 μg/ml of anti-FcγRIIxanti-LDL plus 1.33 μg/ml of BODIPY- LDL, in the presence of 400 μg/ml unlabeled LDL, or 75 μg/ml of unlabeled AcLDL. Cell-associated LDL* was analyzed by flow cytometry as described in "Materials and Methods". Shown are the means±SD of triplicate measurements of cell-associated LDL* from a representative experiment.

Example 6
LDL Degradation Mediated Through FcγR

Figure 4:
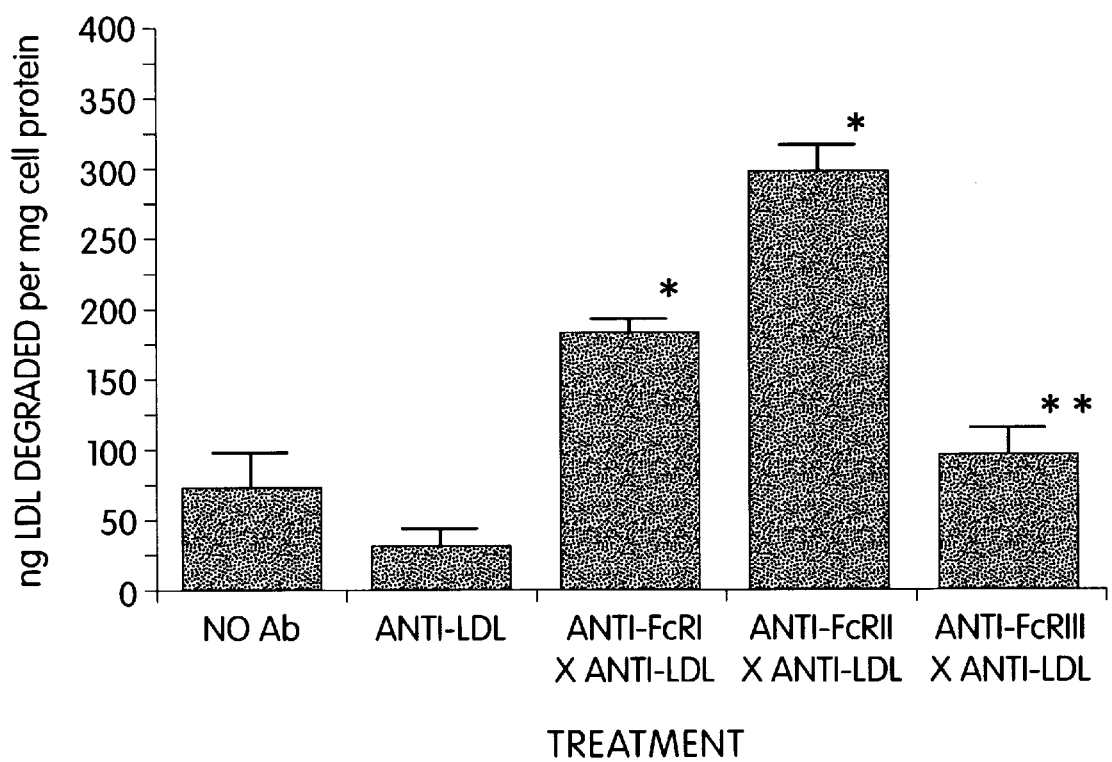
FIG. 4 is a graphic representation of degradation of $^{125}$I-LDL by human monocytes mediated through FcγR. Monocytes in 10% LPDS were treated for four hours at 37° C. with $^{125}$I-LDI, plus saturating amounts of bispecific anti-FcγRI×anti-LDL, anti-FcγRII×anti-LDL, or anti-FcγRIII×anti-LDL. Controls are shown consisting of $^{125}$I-LDL in the absence of antibody, and $^{125}$I-LDL plus an equivalent amount of unconjugated anti-LDL. The cell supernatants were analyzed for acid-soluble products that did not contain free iodide. All values were corrected for spontaneous degradation by subtracting the value of the appropriate cell-free control. Shown are the means±SEM of duplicate measurements from three experiments. "*", significant to both controls; "**", significant to anti-LDL control only.

To determine whether or not uptake of bispecific LDL-IC was associated with metabolic degradation of LDL, monocytes were treated with saturating amounts of $^{125}$I-LDL plus anti-FcγRI×anti-LDL, anti-FcγRII×anti-LDL, or anti-FcγRIII×anti-LDL as described in "Materials and Methods" and incubated for four hours at 37° C. Controls were done consisting of $^{125}$I-LDL alone, and $^{125}$I-LDL plus anti-LDL, both with and without cells. Cell-free degradation of $^{125}$I-LDL with and without antibody were approximately equal; therefore all cell-free control values were averaged to correct for specific degradation mediated with bispecifics. The results of three experiments are summarized in FIG. 4. After correction for cell-free degradation, treatment of monocytes with each type of heteroantibody resulted in degradation of $^{125}$I-LDL that appeared to correlate with the levels of expression of the respective type of FcγR. The most degradation was seen in association with anti-FcγRII×anti-LDL and was significant when compared to both of the controls (4.2 times No Ab and 9.5 times anti-LDL, both p=0.001). Degradation associated with anti-FcγRI×anti-LDL was more than half of that associated with anti-FcγRII×anti-LDL and was also significant when compared to both controls (2.6 times No Ab, p =0.005; 5.9 times anti-LDL, p =0.001). Although freshly isolated monocytes express relatively few binding sites for FcγRIII, LDL degradation was also associated with bispecific anti-FcγRIII×anti-LDL (3.2 times anti-LDL, p=0.05).

Example 7
Metabolic Processing of LDI, via FCγR

To determine the metabolic fate of LDL taken up by monocytes via each Fcγ receptor, monocytes obtained from one individual were treated with saturating amounts of aggregated LDL (an insoluble preparation prepared by vortex aggregation of LDL for 60 seconds) opsonized with anti-FcγRI×anti-LDL, anti-FcγRII×anti-LDL, or anti-Fcγ RIII×anti-LDL as described in "Materials and Methods" and incubated for 24 hours at 37° C. Controls were done consisting of LDL added alone and anti-LDL Fab'$_2$ opsonized LDL. Cells were then harvested and the lipid portion was extracted into chloroform, dried into nitrogen and reconstituted into 2-propanol. The amount of cellular cholesterol and cholesteryl esters in the resulting lipid portion was analyzed by reverse-phase high performance liquid chromatography (HPLC) substantially according to the method of Araki et al. (Araki, N. et al. (1990) *Analytical Biochemistry* 185:339–345), the contents of which are incorporated herein by reference. Briefly, following cell harvesting, chloroform /methanol (2/1 v/v) was added and cellular lipids extracted by a modification of the method of Brown et al. ((1979) *J.Cell. Biol.* 82:597–613). After overnight extraction at 4° C., an organic phase was removed and the aqueous phase was rinsed briefly with 10 ml of chloroform. The organic phases were combined and dried by a stream of $N_2$ gas. Lipid extracts were redissolved in 2-propanol for use in HPLC analyses with a Hewlett Packard liquid chromatograph system and a $C_8$ (3.9 mm×15 cm, 5 μm, 300 Å) reverse phase HPLC column (Waters Associate, USA).

The results of the HPLC analyses on cellular cholesterol and cholesteryl ester mass retained by monocytes following treatment with each type of heteroantibody (i.e., anti-FcγRI× anti-LDL, anti-FcγRII×anti-LDL, and anti-FcγRIII×anti-LDL) indicated that, in cells obtained from at least one individual, a significantly reduced amount of lipid (mg/ml cell protein) was retained by the cells treated with anti-FcγRI×anti-LDL opsonized LDL compared to the other heteroantibodies. Thus, targeting LDL to FcγRI with a bispecific molecule may result in decreased retention of lipids by the cell.

The data suggest that the effects of bispecific LDL*-IC occur independently of native LDL receptors or scavenger receptors that are blocked by AcLDI,. As previously discussed, effects of bispecific LDL*-IC were completely inhibited only by pretreatment of cells with excess anti-FcγR mAb (FIG. 1), and are thus dependent upon binding to Fcγ R. As the uptake of bispecific LDL*-IC relative to LDL* alone was not inhibited by pretreatment of cells with excess unlabeled LDI, or AcLDL (FIG. 4), it is unlikely that FcγR functioned only to fix the complex to the cell surface thereby allowing LDL* to enter via native LDL receptors or scavenger receptors.

It is unlikely for several reasons that treatment of cells with bispecific LDL*-IC caused superoxide production that resulted in I,DL* oxidation and subsequent interaction with scavenger receptors (Cathcart, M. K., et al. (1985) *J. leukocytc Biol.* 38:341–350; Cathcart, M. K., et al. (1989) *J. Immunol.* 142:1963–1969). Most importantly, the presence of antioxidants had no effect on the uptake of bispecific L-DL*-IC over a twenty hour period. The fact that the response to bispecific LDL*-IC was significant by two to four hours of stimulation (FIG. 3) also argues against a major influence of superoxide-induced modification of LDL at least at those time points, as others have shown using human monocytes, that LDL oxidation triggered by superoxide production began six hours after activation with immune complexes (Cathcart, M.K., et al. (1989) *J. Immunol.* 142:1963–1969. Moreover, since blockade of scavenger receptors with AcLDL failed to inhibit the response to bispecific LDL*-IC, it is difficult to envision that superoxide anion-induced modification of LDL* was contributing in a major way in these studies.

Equivalents

Those skilled in the art will recognize, or be able to ascertain using no more than routine experimentation, many equivalents to the specific embodiments of the invention described herein. Such equivalents are intended to be encompassed by the following claims.

I claim:

1. A method of preventing or treating atherosclerosis in an individual, comprising administering to the individual a therapeutic amount of a bispecific molecule, said bispecific molecule comprising:
   (a) at least one first binding specificity for human high density lipoprotein (HDL), or a fragment thereof; and
   (b) at least one second binding specificity for an Fcγ receptor for immunoglobulin G on a human effector cell, wherein said second binding specificity binds Fcγ receptor without being blocked by monomeric immunoglobulin G.

2. The method of claim 1, wherein the first binding specificity is a human HDL-specific antibody or antigen-binding fragment thereof.

3. The method of claim 1, wherein the second binding specificity is an antibody or antigen-binding fragment thereof which binds an Fcγ receptor selected from the group consisting of FcγRI receptor, FcγRII receptor, and FcγRIII receptor.

4. The method of claim 1, wherein the bispecific molecule is a heteroantibody comprising a first antibody or antigen-binding fragment thereof which binds human HDL, and a second antibody or antigen-binding fragment thereof which binds an Fcγ receptor selected from the group consisting of FcγRI receptor, FcγRII receptor, and FcγRIII receptor.

5. The method of claim 4, wherein the heteroantibody comprises a Fab fragment which binds human HDL and a Fab fragment which binds an Fcγ receptor selected from the group consisting of FcγRI receptor, FcγRII receptor, and FcγRIII receptor.

6. The method of claim 1, further comprising administering to the individual a cytokine.

7. A method of enhancing the natural cholesterol transport function of human high density lipoprotein (HDL) in an individual, comprising administering to the individual a therapeutic amount of a bispecific molecule, said bispecific molecule comprising:

(a) at least one first binding specificity for HDL, or a fragment thereof, and (b) at least one second binding specificity for an Fcγ receptor for immunoglobulin G on a human effector cell, wherein said second binding specificity binds Fcγ receptor without being blocked by monomeric immunoglobulin G.

8. The method of claim 7, wherein the first binding specificity is a human HDL-specific antibody or antigen-binding fragment thereof.

9. The method of claim 7, wherein the second binding specificity is an antibody or antigen-binding fragment thereof which binds an Fcγ receptor selected from the group consisting of FcγRI receptor, FcγRII receptor, and FcγRIII receptor.

10. The method of claim 7, wherein the bispecific molecule is a heteroantibody comprising a first antibody or antigen-binding fragment thereof which binds human HDL, and a second antibody or antigen-binding fragment thereof which binds an Fcγ receptor selected from the group consisting of FcγRI receptor, FcγRII receptor, and FcγRIII receptor.

11. The method of claim 10, wherein the heteroantibody comprises a Fab fragment which binds human HDL and a Fab fragment which binds an Fcγ receptor selected from the group consisting of FcγRI receptor, FcγRII receptor, and FcγRIII receptor.

12. The method of claim 7, further comprising administering to the individual a cytokine.

* * * * *